United States Patent [19]

Dyke et al.

[11] Patent Number: 4,594,223

[45] Date of Patent: Jun. 10, 1986

[54] DEVICE FOR DETECTING THE PRESENCE OF NONCONDENSABLE GAS IN STEAM STERILIZERS

[75] Inventors: Denis G. Dyke, Edinboro; David A. Oshlag, Erie, both of Pa.

[73] Assignee: American Sterilizer Company, Erie, Pa.

[21] Appl. No.: 683,818

[22] Filed: Dec. 20, 1984

[51] Int. Cl.⁴ .......................................... G01N 31/22
[52] U.S. Cl. .................................. 422/56; 422/58; 422/119; 436/1
[58] Field of Search ............... 422/55, 58, 56, 119; 436/1

[56] References Cited

U.S. PATENT DOCUMENTS

| 4,115,068 | 9/1978 | Joslyn | 422/56 |
| 4,410,493 | 10/1983 | Joslyn | 422/58 |
| 4,486,387 | 12/1984 | Augurt | 422/58 |

Primary Examiner—Robert Lindsay

Attorney, Agent, or Firm—Robert D. Yeager; Christine R. Ethridge

[57] ABSTRACT

A device for indicating the presence of unacceptable levels of noncondensable gas, such as air, in a stream sterilization chamber. The device includes an insulated heat sink having an upper end and a lower end. The upper end of the heat sink is in such open communication with the sterilization chamber that the steam enters the heat sink. The device also includes a chamber proximate the lower end of the heat sink. The heat sink defines a path through which the steam travels from the upper end toward the chamber. The path is adapted to provide sufficient exposure of the steam to the heat sink so that the steam condenses within the path, releasing any noncondensable gas associated with the steam and forcing it toward the chamber. The chamber includes means for indicating the presence of noncondensable gas accumulated therein. The device also includes means for preventing the condensate from effecting the indicating means.

15 Claims, 6 Drawing Figures

DEVICE FOR DETECTING THE PRESENCE OF NONCONDENSABLE GAS IN STEAM STERILIZERS

BACKGROUND OF THE INVENTION

1. Field of the Invention

The present invention relates to devices for indicating the presence of a noncondensable gas in steam sterilizers.

2. Description of the Prior Art

In prevacuum steam sterilizers, an evacuation stage during which air is removed from the chamber preceeds the sterilization stage during which the pressurized vapor, or steam, is injected into the chamber. Any residual air in the chamber tends to form an insulating shield around items placed in the sterilizer for processing. Such a shield of air may prevent the steam from effectively contacting all portions of the items. Thus, either the inefficient evacuation of the chamber or air leaks in the sterilizer may prevent acceptable sterilization.

In 1963, the Bowie-Dick test was developed for determining the air removal efficiency of prevacuum steam sterilizers. A cross of sterilizer tape is placed at various levels in a pack of muslin towels which, when folded into eight layers, forms a stack approximately 10–11 inches high. If a pocket of residual air forms, the tape registers the air's presence by a lack of change in the indicator. The air insulates the heat and humidity sensitive tape, thereby preventing at least a portion of the tape from undergoing the characteristic color change indicative of successful sterilization.

In place of sterilizer tape, sheets consisting of patterned heat and humidity sensitive indicators are placed midway in the pack of towels. A light spot towards the center of the sheet pattern indicates the presence of an air pocket. The Bowie-Dick pack provides three key parameters for the determination of sterilizer air removal: (1) a sufficient heat sink, (2) insulation properties, and (3) density impeding steam penetration. Upon contacting the pack, steam gives up its latent energy in heating the pack and collapses or condenses back to water. In the pack heat-up process, steam collapses repeatedly until the pack temperature reaches that of steam. In the collapse of steam, a void is created which is instantaneously filled by the surrounding steam. If air is mixed with the steam, the air will remain after each collapse of the steam, thus creating a concentration of air. The Bowie-Dick towel pack also absorbs the condensed steam, adding to its heat sink capacity, and not interfering with the chemical indicator. The towels of the pack themselves are poor heat conductors and are primarily heated through actual steam penetration. The towel pack density limits the heat-up process to a moving front where the pack is heated progressively towards the center rather than uniformly throughout the pack. If an air leak is present or an insufficient vacuum is drawn, during the evacuation stage, air is forced into and/or remains in the pack. In the final stage of the cycle, steam is injected into the sterilizer and the temperature is maintained at about 270° F. At this point, if residual air is still present, it is concentrated toward the center of the pack where it prevents the steam from contacting the indicator. The area of chemical indicator sheet insulated by the air does not change color while the exposed sections turn black.

There is no definite standard for the Bowie-Dick test. Interpretation of the tape or test sheet color gradations is subjective. Furthermore, inconsistent thread count in the muslin towels, variations in pack penetration and laundering can alter the resistance to steam penetration from test to test so the color changes are inconsistent for the same quantities of air. The inconsistent results over time, together with the subjective nature of the interpretation, create a margin of error at critical lower levels of an air leak.

Joslyn U.S. Pat. No. 4,115,068, which issued on Sept. 19, 1978, discloses an air detecting device for steam or gas sterilizers. The Joslyn air detector includes an upright insulated tube, closed at the top and open at the bottom, a heat sink lining the inside of the tube for condensing the steam, and a thermal indicator strip in the tube spaced from the heat sink. Steam enters the tube at the bottom, travels an upward path to the chamber where it is condensed in close proximity to the indicator. The air is entrapped at the top of the tube and the condensate falls down the tube to exit the device. Because the condensate forms in the same chamber in which the indicator strip is located, the condensate can contact the strip. The heat from incoming steam can vaporize the condensate on the strip, thereby interfering with the shielding effect of the air. The penetration gradient in the Joslyn air detector is from bottom to top. Incoming steam must work against gravity, the weight of any accumulated air, which is heavier than steam, and the downward moving condensate.

There is a need for a device for indicating the presence of noncondensable gas, or air, in a steam sterilization chamber which will provide standardized results to reduce the margin of error associated with the prior art tests. There is a further need for such a device which reduces the opportunity for interference with the insulating effect of the noncondensable gas. Finally, there is a need for a device which is sensitive enough to detect critical quantities of air.

SUMMARY OF THE INVENTION

The present invention provides a device adapted for insertion into a steam sterilization chamber for indicating the presence of unacceptable levels of noncondensable gas, such as air. The device includes a heat sink having an upper end and a lower end. The upper end of the heat sink is adapted for such open communication with the sterilization chamber when the device is inserted therein that the steam enters the heat sink. The heat sink is adapted to absorb the latent heat from the steam until the temperature of the heat sink is in equilibrium with the ambient sterilizer temperature. The device also includes a chamber proximate the lower end of the heat sink. The heat sink defines a path through which the steam travels from the upper end toward the chamber. The path is adapted to provide sufficient exposure of steam to the heat sink so that the steam condenses within the path, releasing any noncondensable gas associated with the steam, forcing the noncondensable gas so released toward the chamber and concentrating such gas within the chamber. The device includes means housed within the chamber for indicating the presence of noncondensable gas concentrated therein and means for preventing the condensate formed from the steam from effecting the indicating means.

The preventing means may be adapted to prevent the condensate from entering the chamber. In this embodiment of the present invention, the device may further include an external reservoir in communication with the path and the preventing means may be a first semipermeable membrane separating the chamber from the path through the heat sink. The first membrane is so permeable to gases and so impermeable to liquids that the noncondensable gas enters the chamber and the condensate is directed into the external reservoir. Alternatively, the heat sink is preferably made of an insulating material defining a tortuous path and adapted to absorb the condensate therein. The heat sink is held within a housing having an opening proximate the upper end of the heat sink. The insulating material may include a fibrous material.

In another embodiment, the preventing means may be a member surrounding the indicating means. The member may be a second semipermeable membrane which is adapted to permit the passage of gas but to prevent the passage of liquid therethrough. Alternatively, the member may be a matrix adapted to so absorb the condensate that the condensate is prevented from effecting the indicating means.

The preventing means may be within the chamber. In this embodiment, the chamber is so structured that condensate formed in the path flows by capillary action along the interior walls of the chamber in a spaced relationship from the indicating means. The chamber has an internal reservoir for so collecting the condensate that the condensate is prevented from effecting the indicating means. A hinged member may separate the chamber from the internal reservoir. The hinged member is adapted to permit the passage of condensate into the reservoir but to prevent passage out of the reservoir. Alternatively, a third semipermeable membrane may separate the chamber from the internal reservoir. The third membrane is adapted to permit the passage of condensate into the internal reservoir but to prevent the passage out of the reservoir. Another embodiment includes an absorbent material disposed in the internal reservoir. The condensate is so absorbed into the material that the condensate is prevented from effecting the indicating means.

The indicating means is preferably a heat and humidity sensitive chemical indicator. The chamber is preferably releasably attached to the heat sink. In one embodiment, the heat sink may be a heat conducting material, such as aluminum, surrounded by an insulating material.

BRIEF DESCRIPTION OF THE DRAWINGS

The following detailed description of the preferred embodiment can be better understood if reference is made to the attached drawings in which.

DETAILED DESCRIPTION OF THE PREFERRED EMBODIMENTS

FIGS. 1 through 6 illustrate the preferred embodiments of the device 10 of the present invention. Device 10 is adapted for insertion into a steam sterilization chamber (not shown), and is especially suited to detect the presence of noncondensable gas, such as air, in the sterilization chamber during processing. It is contemplated that device 10 will be used to detect air leaks in the sterilizer or to detect inefficient evacuation in the prevacuum phase of a sterilization cycle.

Figure 1:
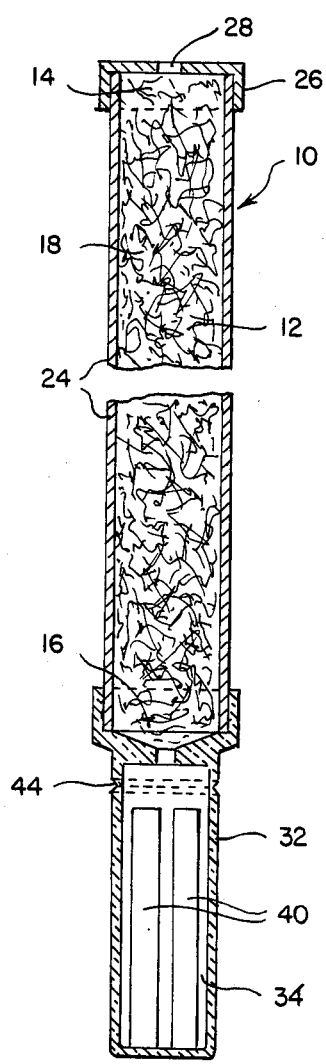
FIG. 1 is a view of the preferred embodiment of the device of the present invention.

Device 10 includes heat sink 12, chamber 34, and indicator strip 40. Heat sink 12 has upper end 14 and lower end 16. Referring to FIG. 1, the preferred embodiment of device 10 includes an elongate tube 24 having a cap 26 adjacent to upper end 14 of heat sink 12. Cap 26 includes opening 28 through which steam enters tube 24 and heat sink 12. Heat sink 12 may be a fibrous insulating material, such as a cellulose fiber. Any material which acts as a heat sink and retains condensate may be used. The fiber acts as a heat sink by absorbing the latent heat from steam which flows through the fiber, as an insulating material by preventing the latent heat from reaching the indicator strip too quickly, and as a means to resist steam penetration.

Path 18, preferably a tortuous path, is defined by the fibrous heat sink 12. Housing 32, which defines chamber 34, is releasably connected to the lower end of tube 24. Path 18 extends from the upper end 14 of heat sink 12 to chamber 34. Path 18 is adapted to provide sufficient exposure of the steam to heat sink 12 to condense the steam within path 18 releasing any noncondensable gas associated with the steam. Such exposure may be achieved by providing a tortuous path or a relatively small diameter for path 18.

Figure 2:
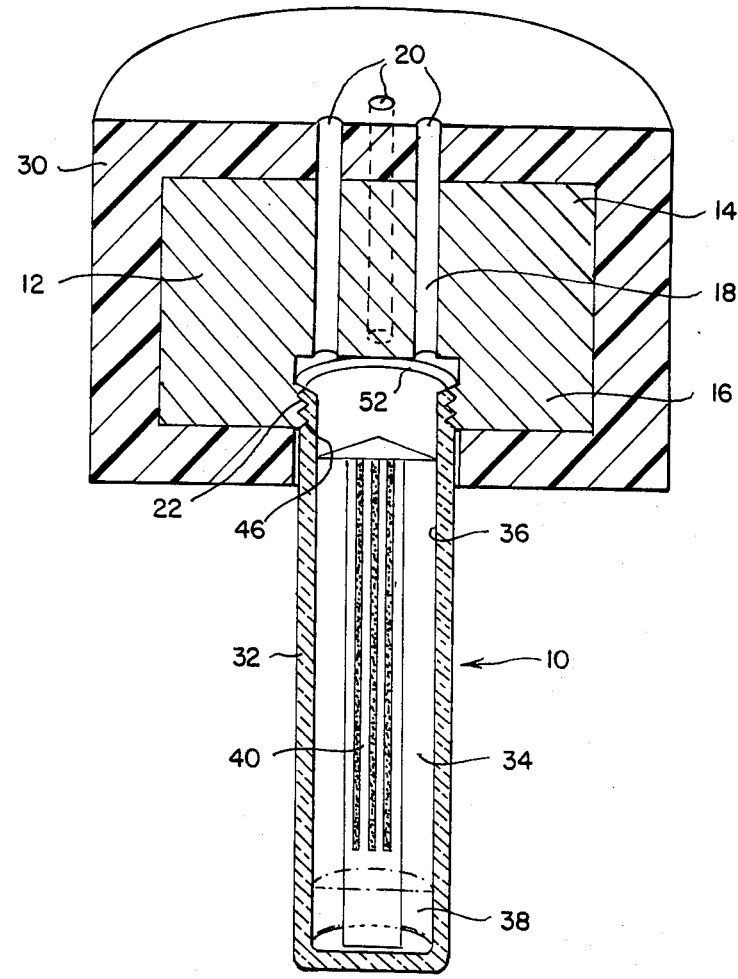
FIG. 2 is a view of an alternative embodiment of the device of the present invention.

There is a weakened, or stressed portion 44 on housing 32 by which the housing 32 can be disconnected from tube 24. Alternatively, as shown in FIG. 2, housing 32 may have a threaded portion 46 for releasably engaging corresponding threaded portion 22 on the heat sink 12 or on a tube 24.

Indicator strip 40 is suspended within chamber 34. Indicator strip 40 is preferably a heat and humidity sensitive indicator which is adapted to change color, for example from white to black, upon exposure to a predetermined temperature and humidity for a period of time. The indicator strip 40 may be any suitable known indicating means which can be employed to indicate the presence of a predetermined level of noncondensable gas, or air, in a given environment.

As the pressure in the sterilization chamber forces steam through opening 28 and through the tortuous path 18 of heat sink 12, the steam repeatedly gives up its latent heat and collapses, or condenses, into water. The collapse of steam creates a partial void along the path 18 containing any noncondensable gases. The void is immediately filled as steam continues to enter the path and the advancing front of steam, together with gravity, concentrates any residual air associated with the steam and forces it toward chamber 34. The advancing front of steam continues to give up its latent heat to the heat sink until the temperature of the heat sink is in equilibrium with the ambient sterilizer temperature.

The air concentrated in chamber 34 will surround indicator strip 40, insulating, or shielding it from exposure to the humidity and latent heat of the steam.

The indicator strip 40 can be calibrated to change color only upon exposure to a quantity of heat and humidity over a period of time which could not be present in the chamber 34 if an unacceptable air leak rate existed. The volume of the chamber 34 can be varied to vary the result in height of the air accumulated in chamber 34 to correspond to a scale for indicating unacceptable levels of air in the sterilization chamber.

Referring to the embodiment of the present invention shown in FIG. 1, the density ratio between the mass of the fibrous insulating heat sink material and the volume of the elongate tube 24 can be controlled to provide a standard resistance to penetration of the material by the steam. The resistance should be such that the steam will condense in the path 18. The condensate so formed will be retained by the fibrous material. It is important that the condensate is separated from the indicator strip 40. If condensate is reevaporated within the chamber 34 in the area of the indicator strip 40, the heat and humidity may effect the accuracy of the strip 40.

If there is a negligible quantity of air associated with the steam, little or no air will accumulate in chamber 34 when the steam condenses. The heat and humidity will contact the indicator strip 40 and cause it to change color during the sterilization stage of the process.

At the end of the sterilization stage, device 10 is removed, housing 32 is broken away from tube 24 along the weakened portion 44 and indicator strip 40 is removed. The strip 40 can be retained as a permanent record for quality control purposes to compare the sterilization cycles over time. Housing 32 is preferably transparent to permit inspection of the indicator strip without the necessity of removing the strip.

In an alternative embodiment of device 10, the heat sink 12 is preferably a metal, for example aluminum, and is surrounded by insulation 30. Referring to FIG. 2, openings 20 in the upper end 14 of heat sink 12 are open to the environment of the sterilization chamber. The steam enters openings 20 and travels through path 18, where the latent heat from the steam is absorbed and condensate forms. The diameter of path 18 should be relatively small to provide sufficient resistance to the flow of steam, thus ensuring sufficient exposure to the heat sink to condense the steam within path 18. Path 18 may also be a tortuous path in the alternative embodiments of device 10.

The condensate may be prevented from entering chamber 34 by means of a semipermeable membrane 52 positioned between chamber 34 and path 18. The membrane 52 may be any suitable membrane which will be permeable to gases but impermeable to liquids. Thus, any residual air will pass through the membrane into chamber 34. An external reservoir (not shown) may be in fluid communication with path 18 at the lower end 16 of heat sink 12 to receive the condensate.

In another embodiment of device 10, the housing 32 may be so structured that the condensate flows into chamber 34 by capillary action along the interior walls 36 of housing 32 in a spaced relationship from indicator strip 40. An internal reservoir 38 is disposed at the bottom of chamber 34 to receive the condensate.

Figure 3:
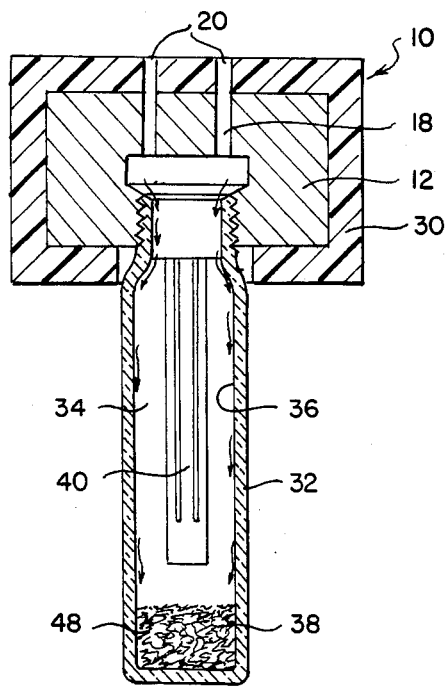
FIG. 3 is a view of the device of FIG. 2 with absorbent material in the internal reservoir.

In order to prevent the condensate collected in reservoir 38 from effecting indicator strip 40, several alternative structures may be employed. The condensate which can detrimentally effect the indicator strip 40, as used herein, refers to condensate in its liquid or reevaporated form. Referring to FIG. 3, an absorbant material 48 may be disposed in reservoir 38.

Figure 4:
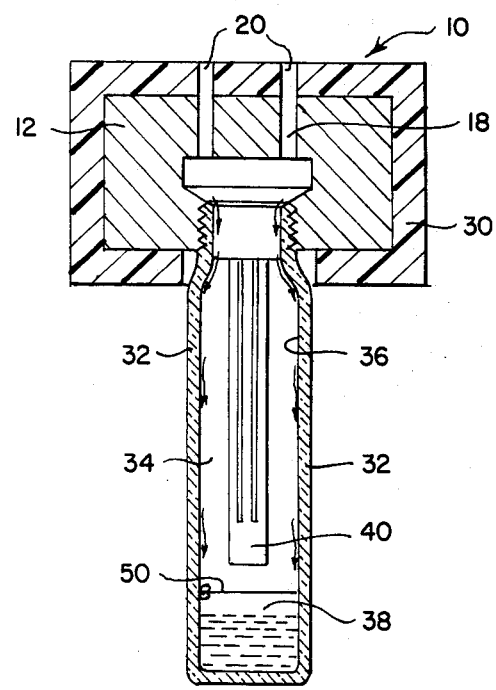
FIG. 4 is a view of the device of FIG. 2 with the hinged member separating the chamber from the internal reservoir.

A hinged member 50, shown in FIG. 4 may separate chamber 34 from reservoir 38. Hinged member 50 may be any suitable member which will permit the passage of condensate into reservoir 38 but which will prevent a reverse passage. An alternative means for separating chamber 34 from reservoir 38 is to place a semipermeable membrane between the two areas, 34 and 38. The membrane must permit the condensate to flow into reservoir 38 but prevent flow in the reverse direction.

Figure 5:
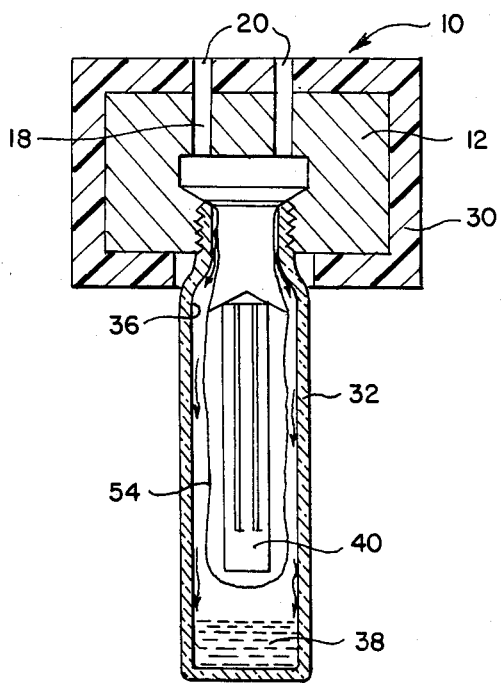
FIG. 5 is a view of the device of FIG. 2 with a membrane surrounding the indicating means.

FIG. 5 illustrates an embodiment of device 10 wherein the indicating strip 40 is loosely surrounded by a semipermeable membrane 54. The air can surround the indicator strip 40 and the condensate can collect in reservoir 38.

Figure 6:
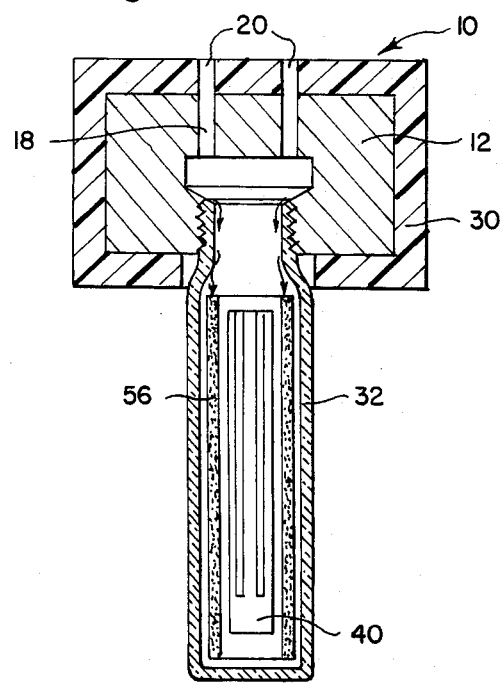
FIG. 6 is a view of the device of FIG. 2 with an absorbent matrix surrounding the indicating means.

FIG. 6 illustrates an alternative embodiment of device 10 which includes a matrix 56 which will absorb or chemically bind liquid to prevent it from effecting the indicator strip 40. The matrix 56 preferably is a hollow, cylindrical affinity chromotographic matrix that will absorb the condensate. Any residual air will be free to pass directly to the indicator strip 40.

The device 10 of the present invention provides a means for more accurately and consistently indicating the presence of noncondensable gas, specifically air, in a sterilization chamber. Because the insulated heat sink 12 and its path 18 superpose the chamber 34 in which the indicator strip 40 is housed and the air accumulates, the necessary condensation occurs before the steam reaches the chamber 34. Gravity and the advancing front of steam force residual air into chamber 34. The greater air concentration and thus, the greater shielding effect of the air around indicator strip 40 permit a progressively greater indication on indicator strip 40.

The arrangement permits a standardized relationship between the mass of the heat sink 12 and the volume of tube 24 so that the effective surface area of path 18, through which the steam travels, is sufficient to condense the steam within the path. A standardized resistance to steam penetration can be established.

What is claimed is:

1. A device adapted for insertion into a sterilization chamber for indicating the presence of unacceptable levels of noncondensable gas comprising:

a heat sink having an upper end and a lower end, said upper end of said heat sink being adapted for such open communication with the sterilization chamber when said device is inserted therein that the steam enters said heat sink, and said heat sink being adapted to absorb latent heat from the steam until the temperature of said heat sink is in equilibrium with the ambient sterilizer temperature;

a housing defining a chamber proximate said lower end of said heat sink;

said heat sink defining a path through which steam travels from said upper end of said heat sink toward said chamber, said path being adapted to provide sufficient exposure of the steam to said heat sink so that the steam condenses within said path, releasing any noncondensable gas associated with the steam, forcing the noncondensable gas so released toward said chamber and concentrating such noncondensable gas within said chamber;

means disposed in said chamber for indicating the presence of noncondensable gas concentrated therein;

means for preventing the condensate formed from the condensed steam from effecting said indicating means but permitting the noncondensable gas concentrated within said chamber to pass to said indicating means.

2. A device as recited in claim 1 wherein said prevention means prevents the condensate from entering said chamber.

3. A device as recited in claim 2 further comprising an external reservoir in communication with said path and wherein said prevention means is a first semipermeable membrane separating said chamber from said path, said first membrane being so permeable to gases and so impermeable to liquids that the noncondensable gas is permitted to enter said chamber and the condensate is directed into said external reservoir.

4. A device as recited in claim 2 further comprising a housing wherein said heat sink is disposed, said housing having an opening proximate said upper end of said heat sink; and said heat sink is an insulating material defining a tortuous path, said insulating material being adapted to so retain the condensate formed within said path that the condensate is prevented from entering said chamber.

5. A device as recited in claim 4 wherein said insulating material includes fibrous material.

6. A device as recited in claim 1 wherein said preventing means is a member surrounding said indicating means.

7. A device as recited in claim 6 wherein said member is a second semipermeable membrane adapted to permit passage of gas but to prevent passage of liquid therethrough.

8. A device as recited in claim 6 wherein said member is a matrix adapted to so retain the condensate that the condensate is prevented from effecting said indicating means.

9. A device as recited in claim 1 wherein said chamber is so structured that condensate formed in said path flows by capillary action along the interior walls of said chamber in a spaced relationship from said indicating means and said chamber has an internal reservoir for so collecting the condensate that the condensate is prevented from effecting said indicating means.

10. A device as recited in claim 9 wherein a hinged member separates said chamber from said reservoir, said hinged member being adapted to permit passage of condensate into said reservoir and to prevent passage from said reservoir to said chamber.

11. A device as recited in claim 9 wherein a third semipermeable membrane separates said reservoir from said chamber, said membrane being adapted to permit passage of condensate into said reservoir and to prevent passage from said reservoir to said chamber.

12. A device as recited in claim 9 wherein said internal reservoir includes an absorbent material wherein the condensate is so absorbed that the condensate is prevented from effecting said indicating means.

13. A device as recited in claim 1 wherein said indicating means is a heat and humidity sensitive chemical indicator.

14. A device as recited in claim 1 wherein said chamber is releasably attached to said heat sink.

15. A device as recited in claim 1 wherein said heat sink is made of a heat conducting material surrounded by an insulating material.

* * * * *

UNITED STATES PATENT AND TRADEMARK OFFICE
CERTIFICATE OF CORRECTION

PATENT NO. : 4,594,223
DATED : June 10 1986
INVENTOR(S) : Denis G. Dyke and David A. Oshlag It is certified that error appears in the above—identified patent and that said Letters Patent is hereby corrected as shown below:

In the ABSTRACT, line 2, delete "stream" and substitute therefor --steam--.

Signed and Sealed this

Twenty-eighth Day of October, 1986

[SEAL]

Attest:

DONALD J. QUIGG

Attesting Officer — Commissioner of Patents and Trademarks